United States Patent
Volpi et al.

(10) Patent No.: US 8,491,595 B2
(45) Date of Patent: Jul. 23, 2013

(54) METHODS AND DEVICES FOR LIGAMENT REPAIR

(75) Inventors: Piero Volpi, Milan (IT); Douglas A. Fifolt, Wrentham, MA (US); Jose E. Lizardi, Franklin, MA (US)

(73) Assignee: DePuy Mitek, LLC, Raynham, MA (US)

( * ) Notice: Subject to any disclaimer, the term of this patent is extended or adjusted under 35 U.S.C. 154(b) by 1286 days.

(21) Appl. No.: 11/862,509

(22) Filed: Sep. 27, 2007

(65) Prior Publication Data

US 2008/0103506 A1    May 1, 2008

Related U.S. Application Data

(60) Provisional application No. 60/855,239, filed on Oct. 30, 2006.

(51) Int. Cl.
*A61B 17/58*    (2006.01)
*A61B 17/60*    (2006.01)
*A61F 2/00*    (2006.01)

(52) U.S. Cl.
USPC .......................................................... 606/96

(58) Field of Classification Search
USPC ............ 606/87, 88, 96, 98; 33/27.02, 27.031, 33/27.032, 27.033
See application file for complete search history.

(56) References Cited

U.S. PATENT DOCUMENTS

| | | | |
|---|---|---|---|
| 4,335,715 A | 6/1982 | Kirkley | |
| 4,744,353 A | 5/1988 | McFarland | |
| 4,898,156 A | 2/1990 | Gatturna et al. | |
| 4,899,743 A | 2/1990 | Nicholson et al. | |
| 4,911,153 A | 3/1990 | Border | |
| 4,968,315 A | 11/1990 | Gatturna | |
| 5,163,940 A | 11/1992 | Bourque | |
| 5,306,278 A | 4/1994 | Dahl et al. | |
| 5,314,429 A | 5/1994 | Goble | |
| 5,324,295 A | 6/1994 | Shapiro | |
| 5,330,468 A | 7/1994 | Burkhart | |
| 5,356,413 A | 10/1994 | Martins et al. | |

(Continued)

FOREIGN PATENT DOCUMENTS

| | | |
|---|---|---|
| EP | 1449484 | 8/2004 |
| FR | 2552655 | 4/1985 |

(Continued)

OTHER PUBLICATIONS

Canadian Examiner's Requisition, Application No. 2,608,464, issued Dec. 3, 2009, 3 pages.

(Continued)

*Primary Examiner* — Nicholas Woodall
*Assistant Examiner* — Christine Nelson

(57) ABSTRACT

Devices and methods are provided for positioning and forming bone tunnels. In one embodiment, a surgical drill guide apparatus is provided. The apparatus can include a first guide member having a longitudinal passageway extending therethrough for aiming a first guide pin along a first path to form a first bone tunnel. The apparatus can also include a second guide member having a longitudinal passageway extending therethrough for aiming a second guide pin along a second path to form a second bone tunnel. The first and second guide members can extend at an angle relative to one another and they can be offset such that axes of the guide members do not intersect.

21 Claims, 9 Drawing Sheets

U.S. PATENT DOCUMENTS

| | | |
|---|---|---|
| 5,372,599 A | 12/1994 | Martins |
| RE36,020 E | 12/1998 | Moore et al. |
| 5,891,150 A * | 4/1999 | Chan .............................. 606/96 |
| 6,022,356 A | 2/2000 | Noyes et al. |
| 6,066,173 A | 5/2000 | McKernan et al. |
| 2003/0220651 A1 | 11/2003 | Pusnik et al. |
| 2004/0082959 A1 | 4/2004 | Hayes et al. |
| 2004/0210232 A1 | 10/2004 | Patel et al. |
| 2005/0143831 A1 | 6/2005 | Justin et al. |
| 2005/0177171 A1 | 8/2005 | Wetzler et al. |
| 2006/0271059 A1 | 11/2006 | Reay-Young et al. |
| 2007/0162122 A1 | 7/2007 | Whittaker |
| 2007/0162123 A1 | 7/2007 | Whittaker et al. |

FOREIGN PATENT DOCUMENTS

| | | |
|---|---|---|
| FR | 2716364 | 8/1995 |
| FR | 2880292 | 7/2006 |
| JP | 63-153057 A | 6/1988 |

OTHER PUBLICATIONS

European Search Report, Application No. 07254277.2, Issued Dec. 4, 2008, 7 pages.

Canadian Examiner's Requisition, Application No. 2,608,464, issued Jul. 21, 2010, 3 pages.

Japanese Office Action for Application No. 2007-280629, issued Jul. 24, 2012. (6 pages).

* cited by examiner

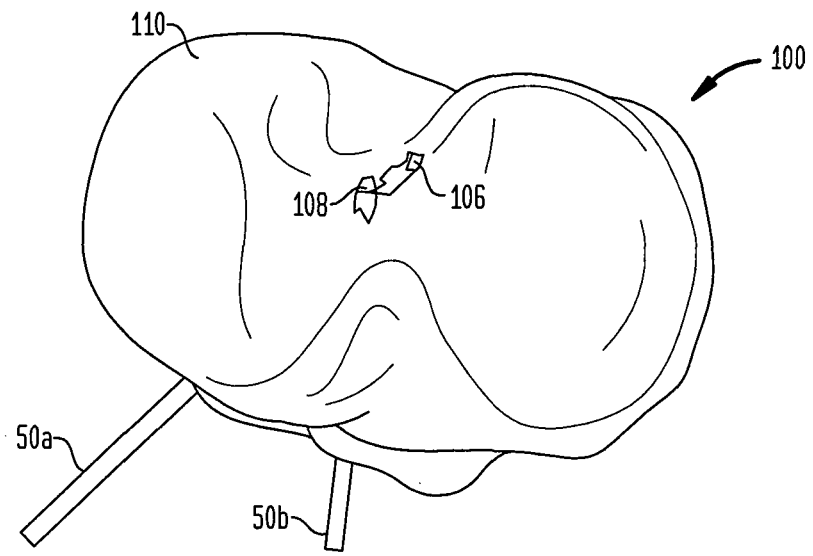

METHODS AND DEVICES FOR LIGAMENT REPAIR

CROSS REFERENCE TO RELATED APPLICATIONS

This application claims priority to U.S. Provisional Patent Application No. 60/855,239 filed Oct. 30, 2006 and entitled "Drill Guide With Multiple Tunnel Capability," which is hereby incorporated by reference in its entirety.

FIELD OF THE INVENTION

The present invention generally relates to surgical methods and devices, and more particularly to instruments and methods for use in knee reconstruction to repair torn ligaments and procedures for such reconstructions.

BACKGROUND

Joint injuries may commonly result in the complete or partial detachment of ligaments, tendons and soft tissues from bone. Tissue detachment may occur in many ways, e.g., as the result of an accident such as a fall, overexertion during a work-related activity, during the course of an athletic event, or in any one of many other situations and/or activities. These types of injuries are generally the result of excess stress or extraordinary forces being placed upon the tissues.

In the case of a partial detachment, commonly referred to under the general term "sprain," the injury frequently heals without medical intervention, the patient rests, and care is taken not to expose the injury to undue strenuous activities during the healing process. If, however, the ligament or tendon is completely detached from its attachment site on an associated bone or bones, or if it is severed as the result of a traumatic injury, surgical intervention may be necessary to restore full function to the injured joint. A number of conventional surgical procedures exist for re-attaching such tendons and ligaments to bone.

One such procedure involves the re-attachment of the detached tissue using "traditional" attachment devices such as staples, sutures, and bone screws. Such traditional attachment devices have also been used to attach tendon or ligament grafts (often formed from autologous tissue harvested from elsewhere in the body) to the desired bone or bones. In one procedure, a damaged anterior cruciate ligament ("ACL") is replaced in a human knee. Initially, bone tunnels are formed through the tibia and femur at the points of normal attachment of the ACL. Next, a ligament graft with a bone graft on one of its ends is sized so as to fit within the bone tunnels. Suture is then attached to the bone graft and thereafter passed through the tibia and femoral bone tunnels. The bone graft is then pulled through the tibial tunnel and up into the femoral tunnel using the suture. As this is done, the ligament graft ligament extends back out of the femoral tunnel, across the interior of the knee joint, and then through the tibial tunnel. The free end of the ligament graft ligament resides outside the tibia, at the anterior side of the tibia. Next, a bone screw is inserted between the bone graft and the wall of femoral bone tunnel so as to securely lock the bone graft in position by a tight interference fit. Finally, the free end of the ligament graft ligament is securely attached to the tibia.

In another ACL reconstruction procedure, aligned femoral and tibial tunnels are initially formed in a human knee. A bone graft with a ligament graft attached thereto is passed through the tunnels to a blind end of the femoral tunnel where the block is fixed in place by an anchor. The ligament extends out of the tibial tunnel, and the end is attached to the tibia cortex by staples or the like. Alternatively, the end of the ligament may be fixed in the tibial tunnel by an anchor or by an interference screw. Various types of ligament and/or suture anchors for attaching soft tissue to bone are also well known in the art. A number of these devices are described in detail in U.S. Pat. Nos. 4,898,156, 4,899,743, 4,968,315, 5,356,413, and 5,372,599, all of which are commonly assigned to Mitek Surgical Products, Inc., a Johnson & Johnson company, and which are incorporated by reference in their entirety.

Alternatively, an ACL reconstruction procedure may be performed where instead of reconstructing the dual bundle structure of the native ACL with the functional equivalent of a single band graft, two bone grafts can be used, each graft in an individual bone tunnel. Such an "anatomic" or double-tunnel procedure traditionally involves freehandedly positioning the two tunnels in the tibia and femur. Forming the two tunnels in the correct positions can be technically challenging, time consuming, and have little consistency or reproducibility in tunnel placement from patient to patient.

Accordingly, there is a need for improved methods and devices for repairing ligaments and for positioning and forming bone tunnels.

SUMMARY

In one embodiment, a surgical drill guide apparatus is provided. The apparatus can include a first guide member having a longitudinal passageway extending therethrough for aiming a first guide pin along a first path to form a first bone tunnel, and a second guide member having a longitudinal passageway extending therethrough for aiming a second guide pin along a second path to form a second bone tunnel. The first and second guide members can be coupled to one another via an elongate support such that the first and second guide members extend at an angle relative to one another and are offset such that axes of the guide members do not intersect. In one exemplary embodiment, the support is an arcuate support that is fixedly mated to the first guide member and slidably mated to the second guide member. A plurality of markings can be formed on the arcuate support for indicating the angle between the first and second guide members.

In another embodiment, the apparatus can include a tibial engagement member having a proximal end coupled to the first guide member and having a distal end adapted to indicate an exit location of first and second bone tunnels formed along the first and second paths. The tibial engagement member can include a slider arm coupled to the first guide member and a probe arm slidably disposed along the slider arm. The distal end of the tibial engagement member can be formed on the probe arm.

The apparatus can also include a first drill guide mounted in the longitudinal passage of the first guide member and a second drill guide mounted in the second longitudinal passage of the second guide member. Markings can be formed on the first and second drill guides. The markings can indicate a depth of a bone tunnel formed by drill bits disposed through the first and second drill guides. The first and second guide members can also each include a locking mechanism for locking a drill guide slidably disposed therethrough in a fixed longitudinal position.

In another embodiment, a surgical drill guide apparatus is provided having a first guide member with a first longitudinal guide passage adapted to receive a drill guide pin therein to form a bone tunnel. A first support arm can be coupled to and can extend horizontally from the first guide member. In one embodiment, the first support arm can be fixedly mated to the first guide member. The first support arm can also have at least one arcuate section. The apparatus can also include a second guide member having a second longitudinal guide passage adapted to receive a drill guide pin to form a bone tunnel. The second guide member can be slidably disposed along the at least one arcuate section of the first support arm to form a variable angle relative to the first guide member. The second guide member can also include a locking element adapted to lock the second guide member in a position on the at least one arcuate section. In some embodiments, the first and second guide members each have a longitudinal axis, and the axes do not intersect. The apparatus can also include a first drill guide mounted in the first longitudinal guide passage and a second drill guide mounted in the second longitudinal guide passage. In another embodiment, the apparatus can include a second support arm coupled to and extending vertically from the first guide member, and an engagement member slidably mounted to the second support arm. The second support arm can be fixedly mated to the first guide member, and it can have at least one arcuate portion. In one exemplary embodiment, the engagement member has a distal tip adapted to indicate an exit location of bone tunnels formed by drill bits disposed through the first and second guide members.

In other aspects, methods for repairing ligaments are provided. In one embodiment, a method can include positioning a first guide member adjacent to bone such that the first guide member is configured to aim a first guide pin through the bone along a first pathway. The method can further include positioning a second guide member adjacent to the bone such that the second guide member can aim a second guide pin through the bone along a second pathway. The method can also include slidably moving the second guide member along an arcuate support arm coupled to the first guide member to adjust an angular orientation of the second guide member relative to the first guide member. The method can also include inserting first and second guide pins through the first and second guide members to form first and second bone tunnels that converge toward one another but that have axes that do not intersect. In some embodiments, the method can also include locking the second guide member in a fixed position along the arcuate support after slidably moving the second guide member. The method can also include sliding at least one of the first and second guide pins longitudinally through at least one of the first and second guide members to adjust a depth of at least one of the first and second bone tunnels to be formed.

In other embodiments, positioning the first and second guide members can include positioning a distal tip of an engagement member coupled to the first guide member at an intended exit location of first and second bone tunnels to be formed along the first and second pathways. In some embodiments, the distal tip is formed on a probe arm slidably coupled to a support arm mated to the first guide member. The method can further include slidably moving the probe arm along the support arm to adjust a position of the probe arm.

BRIEF DESCRIPTION OF THE DRAWINGS

The invention will be more fully understood from the following detailed description taken in conjunction with the accompanying drawings, in which:

FIG. 5 is top view of the tibia of FIG. 4 showing drill tips exiting an upper end of the tibia;

FIG. 6 is a table showing various tunnel offsets using various sized drill guides with the instrument of FIG. 1;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope is defined solely by the claims. The features illustrated or described in connection with one exemplary embodiment may be combined with the features of other embodiments. Such modifications and variations are intended to be included within the scope of the present application.

The present invention generally provides methods and devices for repairing ligaments and for positioning and forming bone tunnels. The various methods and devices disclosed herein can be used in a variety of surgical procedures, however the methods and devices are particularly useful for repairing an anterior cruciate ligament ("ACL") in a human knee. In an ACL repair, the torn ACL can be replaced with two ligament grafts which are each anchored to the tibia and femur. The term "ligament graft," as used herein, is intended to include natural materials, such as autografts, allografts, and xenografts, including harvested ligaments and tendons, as well as synthetic materials. A ligament graft can also include an anchoring element attached thereto for anchoring the graft to the tibia and femur. For example, the ligament graft can include a bone graft, plug, or other member, attached to one or both terminal ends thereof. The term "bone graft," as used herein, in intended to include natural materials, such as autografts, allografts, and xenografts, as well as synthetic materials. A person skilled in the art will appreciate that the various methods and devices disclosed herein can be used in a variety of surgical procedures, and that the particular configuration of the ligament grafts can vary depending on the intended use, and virtually any ligament grafts known in the art can be used with the devices and methods disclosed herein.

Figure 1:
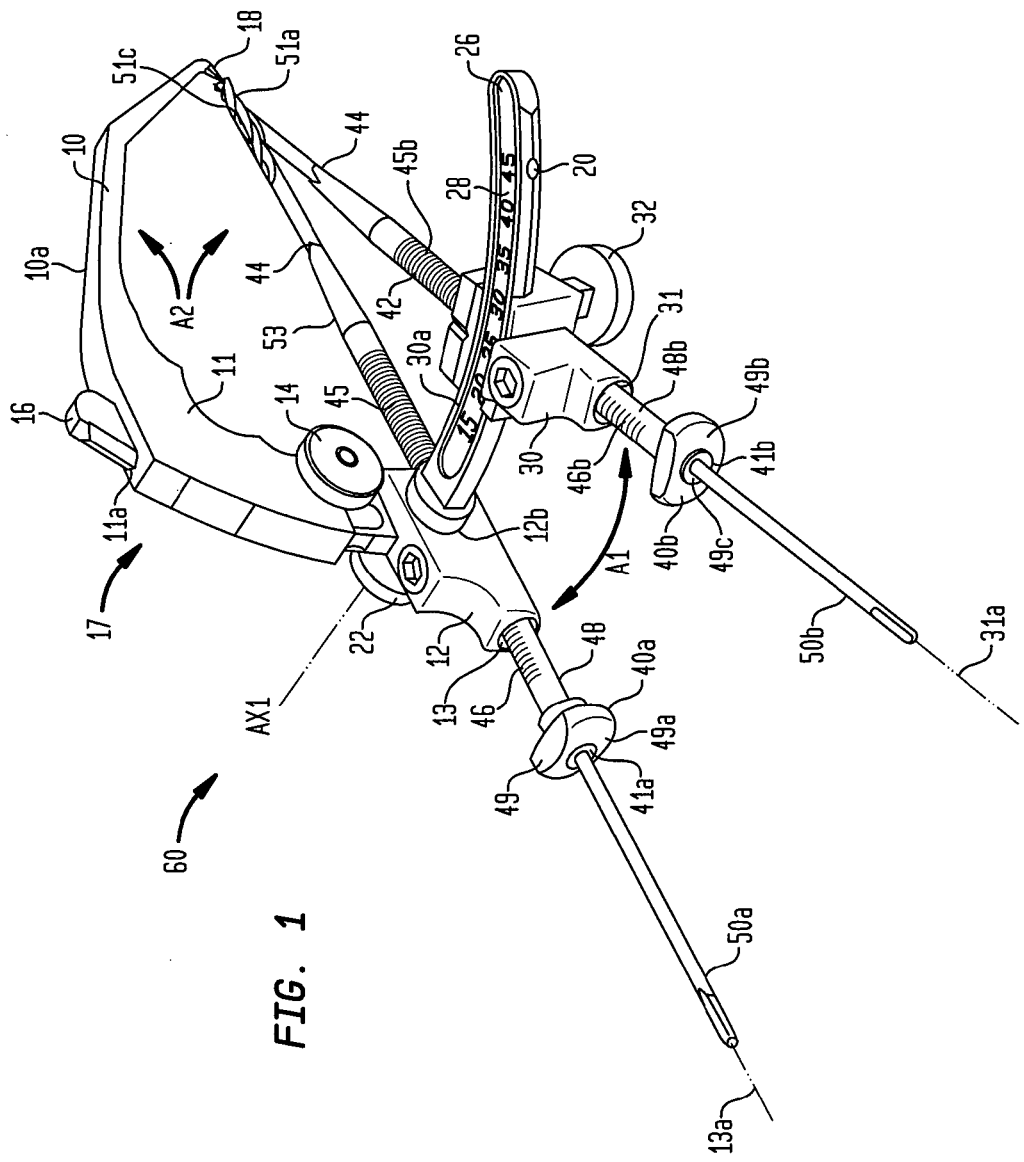
FIG. 1 is a perspective view of one exemplary embodiment of an instrument useful in drilling tunnels in bone in a ligament reconstruction procedure.

FIG. 1 illustrates one exemplary embodiment of a surgical drill guide instrument 60. In general, the instrument 60 allows for placement of multiple tibial tunnels. As shown, the instrument 60 generally includes first and second guide members 12, 30 connected together via a support or outrigger arm 26. The guide members 12, 30 can be angularly adjustable relative to one another to form an angle A1 therebetween that defines an insertion trajectory of two bone tunnels to be formed. The instrument 60 can also include first and second guide pin sleeves or drill guides 40a, 40b slidably disposable through guide channels 13, 31 formed in the guide members 12, 30. The drill guides 40a, 40b can be configured to receive drill bits therethrough for drilling bone tunnels in bone. As further shown in FIG. 1, the instrument 60 can also optionally include a tibial engagement member 17 that is coupled to one of the guide members, e.g., the first guide member 12, and that is adapted to engage a tibial plateau to indicate an exit location of the first and second bone tunnels. In use, the instrument 60 can allow for adjustable placement of tunnel entrance points on the tibial cortex and for adjustable offset of tunnel exit points on the tibial plateau. The placement and offset can also be recorded using the instrument 60, thereby allowing time-saving reproduction of multiple tunnels.

The guide members 12, 30 can each have a variety of configurations, but in the illustrated embodiment each guide member 12, 30 generally includes a housing and a pathway. The housings and the pathways can have a variety of shapes, but they are preferably configured to receive a drill guide or other drilling apparatus. In the illustrated embodiment each housing is generally rectangular and each pathway 13, 31 is generally cylindrical for slidably receiving a generally cylindrical drill guides 40a, 40b, as will be discussed further below. The guide members 12, 30 can each also include a locking mechanism for locking the drill guides 40a, 40b in position within the guide members 12, 30. In one exemplary embodiment, each locking mechanisms is in the form of a conventional ratchet having a pawl that engages teeth formed on the guide members. A person skilled in the art will appreciate that a variety of other locking mechanisms known in the art can be used to allow the guide members to be locked in a fixed positioned relative to the guide members 12, 30.

Each of the guide members 12, 30 can also be angularly adjustable relative to one another. While various techniques can be used for allowing angular adjustability, in an exemplary embodiment, as shown, the guide members 12, 30 are coupled to one another via the support or outrigger arm 26. The outrigger arm 26 can be a generally elongate member, and in an exemplary embodiment all, or at least a portion of, the elongate member is arcuate. The outrigger arm 26 can be movably coupled to the first and second guide members 12, 30, or one of the guide members 12, 30 can be fixed relative to the outrigger arm 26 while the other guide member 12, 30 is movable. In the illustrated embodiment, the outrigger arm 26 is mated to the first guide member 12 in a transverse, keyed thru-hole 12b located in the side of the first guide member 12 such that the outrigger arm 26 can extend horizontally from the first guide member 12. Preferably, the outrigger arm 26 is fixedly mated to the first guide member 12 and secured via a thumbscrew 22. In other embodiments, however, the outrigger arm 26 can be rotatably, but non-slidably mated to the first guide member 12.

The outrigger arm 26 can slidably couple to the second guide member 30 in a slot 30a formed in the second guide member 30. The slot 30a can have virtually any configuration, and in this embodiment it is a generally rectangular arcuate channel that can removably seat the arcuate outrigger arm 26. The second guide member 30 can thus slidably move along the outrigger arm 26 until positioned at a desired angle A1 relative to the first guide member 12. Once positioned as desired, the second guide member 30 can be secured in position using a conventional locking mechanism, such as a thumbscrew 32. As further shown in FIG. 1, the outrigger arm 26 can optionally include external markings 28 that indicate the angle A1 between the first and second guide members 12, 30.

As indicated above, the outrigger arm 26 can be oriented in a vertical direction about an axis AX1 relative to the first guide member 12 to achieve an offset between the longitudinal axes 13a, 31a of the guide channels 13, 31 and hence the drill guide channels 41a, 41b and bone tunnels that may be drilled following them. In an exemplary embodiment, the instrument 60 can include multiple outrigger arms (each similar to the outrigger arm 26) that can be keyed to different rotational positions within the slotted thru-hole 12b on the first guide member 12. The multiple outriggers can be keyed with a series of slot patterns to maintain the ability to use a single outrigger with a given offset on both the left and right side of the first guide member 12, or individual left and right outrigger arms can be constructed for each desired offset position. The multiple outrigger arms could be fixed in position within the thru-hole 12b. A locking mechanism, such as the thumbscrew 22 as shown, can optionally be used. In other embodiments, as previously explained, the outrigger arm 26 can be rotatably but non-slidably mated to the first guide member 12. The offset of the outrigger arm 26 can be adjusted (i.e., either rotationally or by selecting an outrigger arm having a predetermined offset) and secured following advancement of the first guide pin 50a through the drill guide 40a (and prior to advancement of a second guide pin 50b, described further below) to help visually gauge a desired offset, or the offset is adjusted and secured at any point prior to placement of the guide pin 50a in the guide sleeve 40a. An additional guide pin positioned through a hole 20 in the outrigger arm 26 can be used as an offset positional reference and/or to provide additional support to the outrigger arm 26, as further described below.

Figure 2:
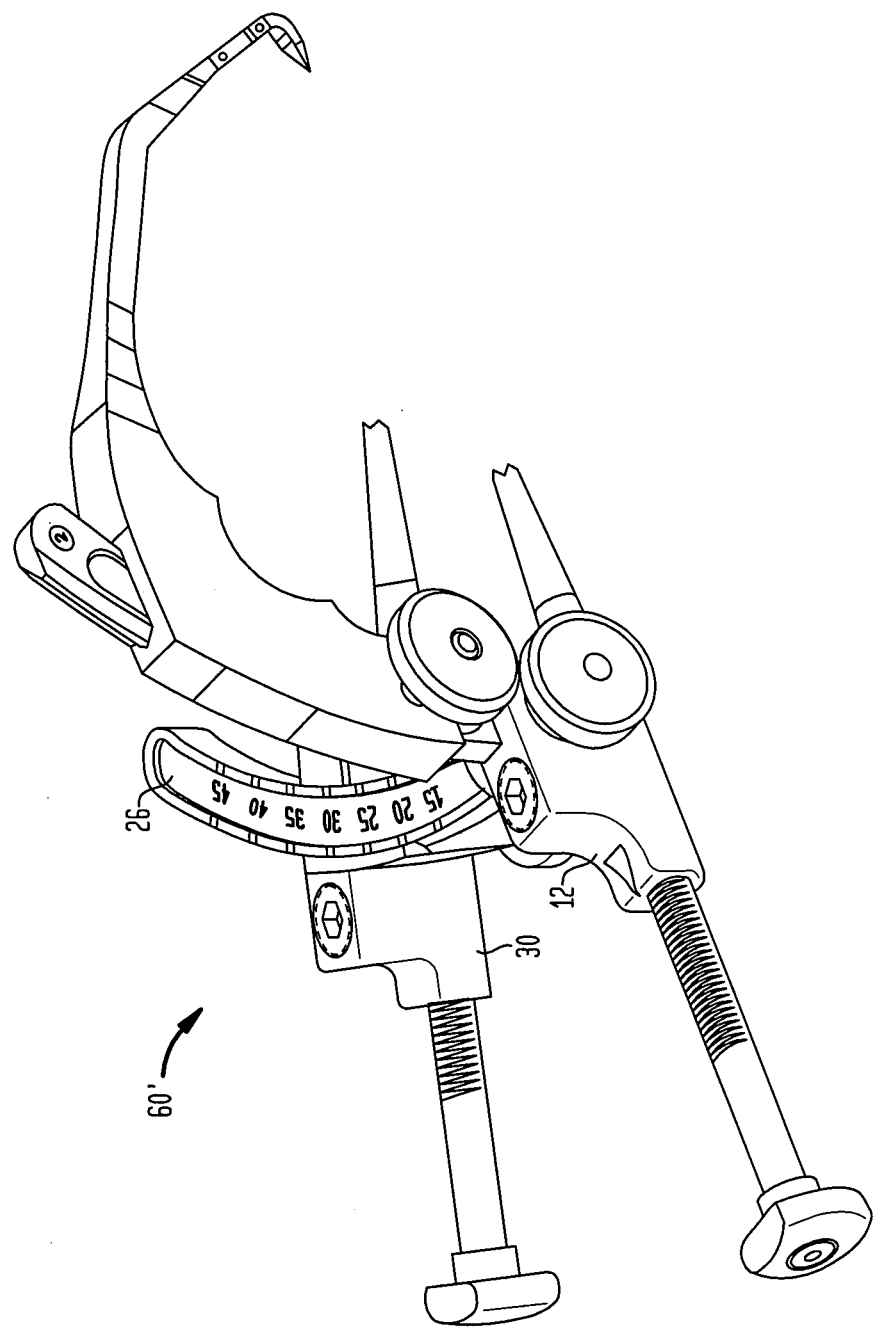
FIG. 2 is a perspective view of another exemplary embodiment of an instrument useful in drilling tunnels in bone in a ligament reconstruction procedure.

FIG. 1 shows the outrigger arm 26 on a right side of the first guide member 12, but the outrigger arm 26 can be located on a left side of the first guide member 12, as shown in another embodiment of an instrument 60' in FIG. 2. The instruments 60, 60' are configured to accommodate the anatomies of the left and right knees, respectively.

Referring still to FIG. 1, the first and second drill guides 40a, 40b that are disposable through the guide channels 13, 31 in the guide members 12, 30 can also have a variety of configurations. In an exemplary embodiment, each drill guide 40a, 40b has a generally elongate tubular configuration, such as a cylindrical shape for receipt in the cylindrical guide channels 13, 31, as shown. This will allow the drill guides 40a, 40b to guide drill bits or any other bone drilling devices disposed in the drill guides 40a, 40b through the guide members 12, 30 and into bone. The drill bits or other bone drilling devices may be directly disposed in the guide channels 13, 31 without the drill guides 40a, 40b. In an exemplary embodiment, as shown, the first drill guide 40a has external markings 46 at its proximal end 48, external teeth 45 or other surface features at its mid-portion or adjacent to its distal end 53, and a center channel 41a extending therethrough between the proximal and distal ends 48, 53 thereof. The first drill guide 40a can be disposed in the first guide member 12 through the channel 13, parallel to the first drill guide's channel 41a. As mentioned above, the teeth 45 can be engaged by a locking mechanism within the channel 13 to allow movement of the first sleeve 40a in a forward or distal direction between a plurality of fixed positions. The first sleeve 40a can also include a bone-engaging distal end, such as teeth 44 formed thereon that engage bone at a desired bone tunnel entrance location, as described further below. The external markings 46 on the first drill guide 40a can indicate an estimated depth of the tunnel with, for example, depth lines printed, embossed, etched, or otherwise marked on the first drill guide 40a that can advance into the channel 13 with the sleeve 40a.

As further shown in FIG. 1, the first drill guide 40a can also include a first annular knob handle 49 mounted or otherwise coupled to the proximal end 48 of the first drill guide 40a for grasping the drill guide 40a and facilitating movement relative to the guide channel 13. The knob handle 49 can include an opening 49a through which a tool or device can be inserted to turn or otherwise manipulate the handle 49 to distally advance the sleeve 40a.

The second guide pin sleeve or drill guide 40b can be configured and manipulated similar to the first drill guide 40a and it can include external markings 46b at its proximal end 48b, external teeth 45b or other surface features at its midportion or adjacent to its distal end 42, a center channel 41b, and a knob handle 49b having an opening 49c. The second drill guide 40b is typically disposed in and advanced through the second guide member 30 after the first drill guide 40a has been disposed in and advanced through the first guide member 12, but the drill guides 40a, 40b can be disposed in and advanced through the guide members 12, 30 in any order.

As previously indicated, the device 60 can also optionally include a tibial engagement member 17 that is effective to engage the tibial plateau and indicate an exit location for guide pins 50a, 50b (and/or other devices used to form the bone tunnels) disposed through the drill guides 40a, 40b. The tibial engagement member 17 can have a variety of configurations, but in the illustrated embodiment it include a slider arm 16 and a probe arm 10. The slider arm 16 can be arcuate or straight and it can include a plurality of connected, angulated straight and/or curved segments. In this embodiment, the slider arm 16 has a generally arcuate orientation extending vertically from the first guide member 12, i.e., offset 45° from the outrigger arm 26. The slider arm 16 can, however, have an arcuate portion and a straight portion, or any other orientation. The probe arm 10 generally includes an elongate body that can be adjustably or slidably mounted to the slider arm 16 through a passage 11a formed in a handle portion 11 of the probe arm 10. The probe arm 10 can also include a distally extending arm portion 10a including a distal tip 18. The distal tip 18 is preferably angulated proximally (e.g., toward a direction of an approaching guide pin), but it can have a distal orientation, both proximal and distal angulations, or neither proximal and distal orientations.

Figure 3:
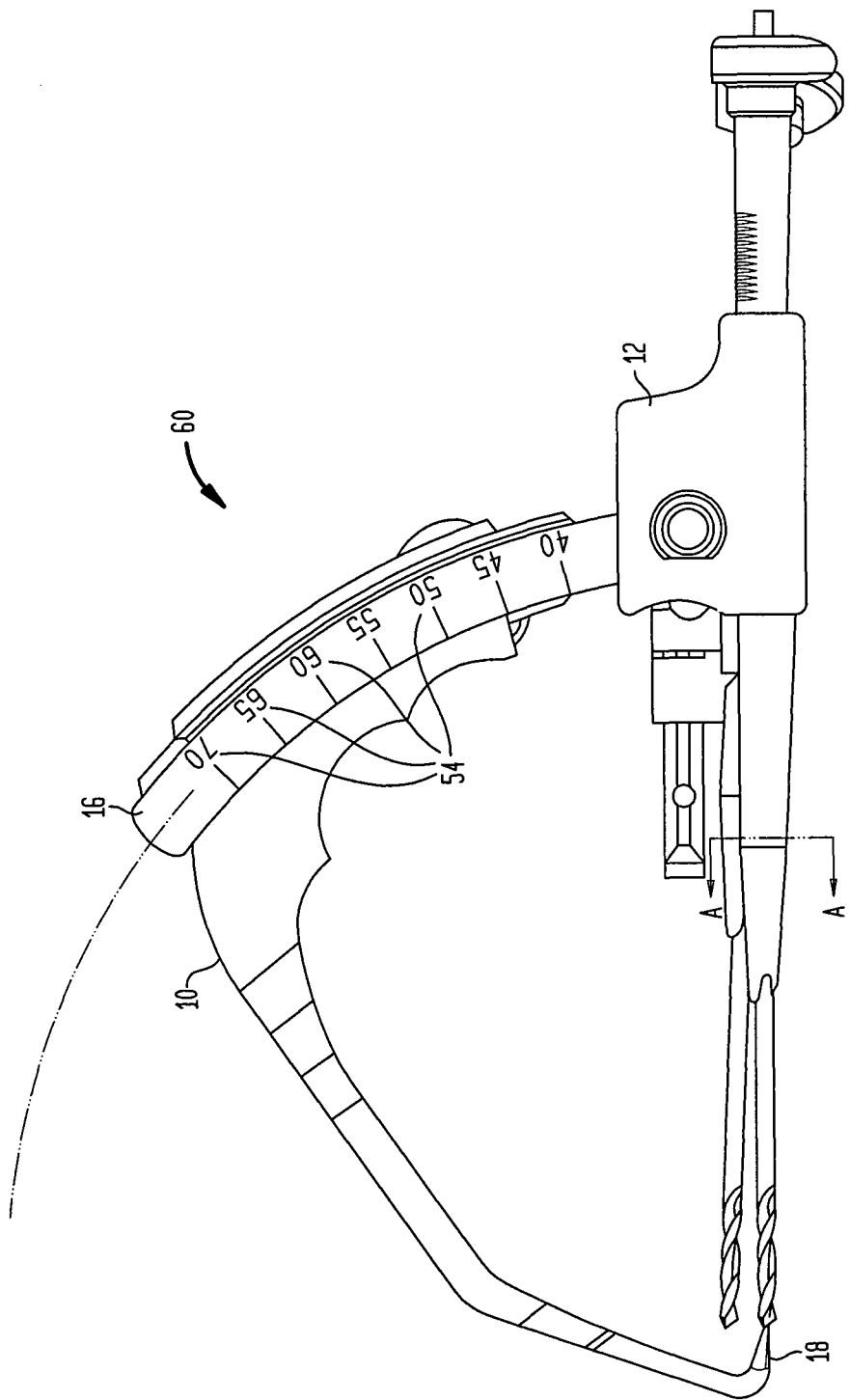
FIG. 3 is a perspective side view of the instrument of FIG. 1.

A position of the probe arm 10, and hence the distal tip 18 and desired endpoint of a bone tunnel, can be slidably adjusted on the slider arm 16 to form an angle A2 between the arm portion 10a of the probe arm 10 and the first guide pin 50a (and the first drill guide 40a). FIG. 3 shows the slider arm 16 slidably mounted to the probe arm 10. External markings 54 on the slider arm 16, which can be printed, embossed, etched, or otherwise marked on the slider arm 16, can indicate the A2 angular position of the probe arm 10. The probe arm 10 can be fixed in position to form a desired angle A2 by, for example, using a conventional locking mechanism such as a thumbscrew 14 coupled to the handle portion 11 of the probe arm 10 and adapted to engage the slider arm 16. The probe arm 10 is typically adjusted to a desired position on the slider arm 16 prior to advancing the guide pin 50a through bone, although the probe arm 10 can be adjusted at any point or points during a ligament repair procedure.

FIG. 1 also illustrates first and second drill tipper guide pins 50a, 50b which can be used with the guide device 60. The first drill tipped guide pin 50a can be disposed through the center channel 41a of the first guide sleeve 40a and advanced distally beyond the teeth 44 of the first guide sleeve 40a and toward the distal tip 18 of the probe arm 10. The first guide pin 50a can be advanced in any known manner, for example, by coupling the guide pin 50a to a conventional surgical drill or driver and advancing the guide pin 50a through the first drill guide 40a and into bone. The guide pin 50a can be advanced through bone, as further described below, until a distal tip 51a of the guide pin 50a is proximate to the tip 18 of the probe arm 10. The drill guide pin 50a can be removed from the drill chuck of the surgical drill and left in place. Similar to that described above regarding the first guide pin 50a, the second guide pin 50b can be advanced through the second drill guide 40b with its distal tip 51c approaching the distal tip 18 of the probe arm 10. A person skilled in the art will appreciate that a variety of other drilling devices can be used, and guide pins 50a, 50b are merely shown for example.

Figure 4:
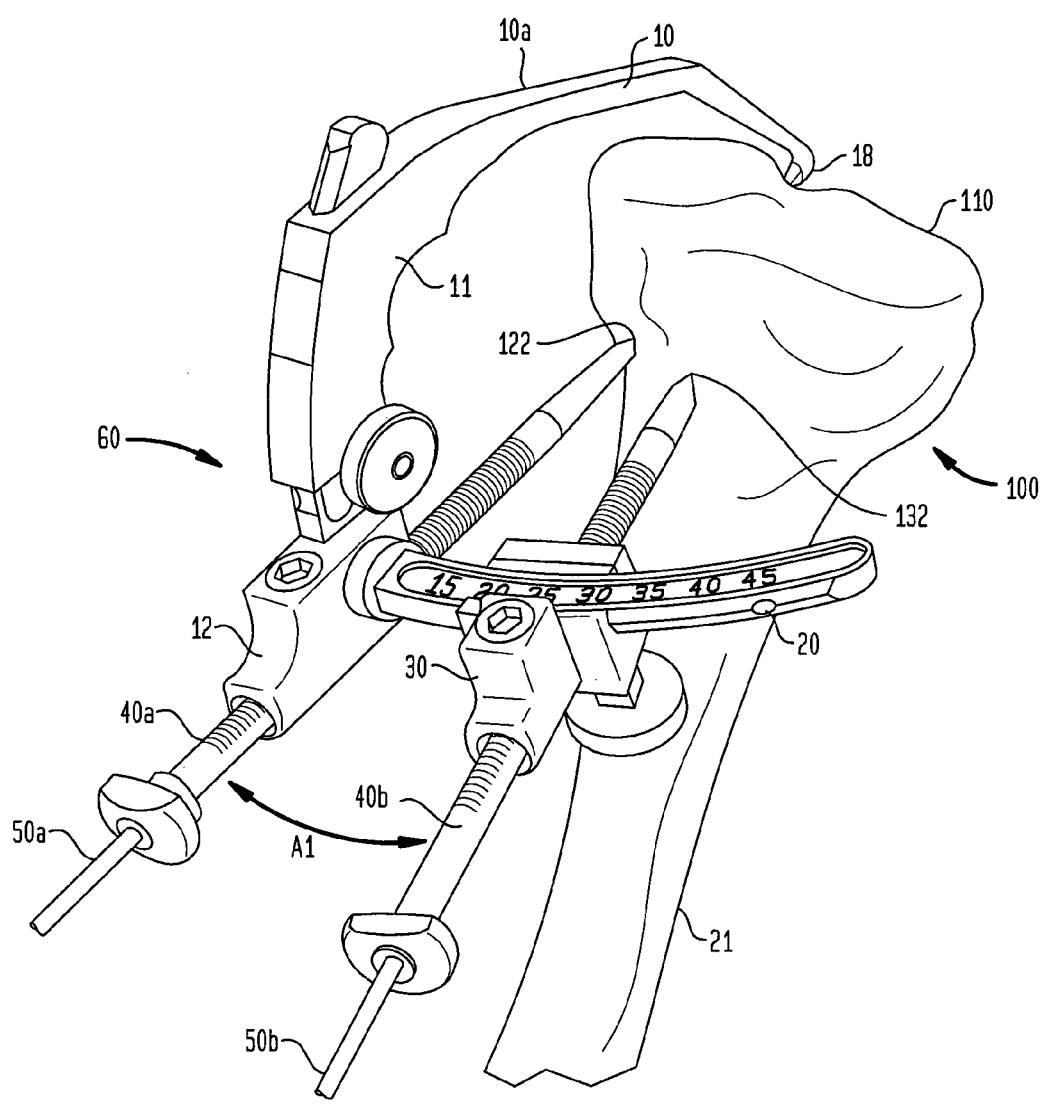
FIG. 4 is a perspective view of the instrument of FIG. 1 engaging an upper end of a tibia and showing a tip of the instrument's probe arm engaging a tibial plateau.

In another aspect, a method for repairing ligaments can be performed using a surgical drill guide apparatus, such as the instrument 60 of FIG. 1. FIG. 4 illustrates one exemplary method for forming bone tunnels for ligament grafts in a surgical procedure, and in particular dual tibial tunnels of a human knee in an arthroscopic procedure. The first guide member 12 can be positioned adjacent to a bone, e.g., the tibia 100, such that the first guide member 12 can aim the first guide pin 50a through the tibia 100 along a first pathway, e.g., the first longitudinal axis 13a extending through the first guide member 12 and the first drill guide 40a. Positioning the first guide member 12 can include inserting the distal portion 10a of the probe arm 10 through an arthroscopic portal (although the instrument 60 can also be used in an open procedure) and orienting it such that the distal tip 18 of the probe arm 10 can engage a section of a tibial plateau 110 of the tibia 100 at an intended tibial tunnel exit point. The first drill guide 40a can be advanced until the guide sleeve distal teeth 44 engage the cortical bone of the tibia 100 at a desired tibial tunnel entrance location 122. The drill-tipped guide pin 50a can be inserted through the center channel 41 of the first guide pin sleeve 40a, mounted to a conventional surgical drill driver, and advanced through the tibial bone 100 using the surgical drill/driver so that the tip 51a of the pin 50a is proximate to the tip 18 of the probe arm 10 on the tibial plateau 110 and indicates intended tunnel depth. The first guide pin 50a can be inserted through the first guide member 12 at any point during the procedure, but it is typically inserted after the first guide member 12 has been positioned at the tibia 100 and before the second guide member 30 has been positioned at the tibia 100.

To form a second bone tunnel, the second guide member 30 can be positioned adjacent to the tibia 100. Positioning the second guide member 30 can include inserting the outrigger arm 26 through the thru-hole 12b of the first guide member 12. Adjustment of the location of the second guide member 30 on the outrigger arm 26 determines the relative positions of the tibial tunnel entrance points to one another, while the vertical offset of the outrigger arm 26 determines the relative vertical offset of the tibial tunnel entrance points. A rotational position of the outrigger arm 26 about the axis AX1 can be adjusted to orient the vertical offset between the two tibial tunnels. In this embodiment, an additional guide pin 21 has been inserted through a thru-hole 20 in the outrigger arm 26 at a 45° angle position on the outrigger arm 26 to act as a position reference with respect to the tibial crest and to help correctly determine the offset. Once at a desired vertical offset, the outrigger arm 26 can be secured in position using the thumbscrew 22. If the second guide member 30 is not already secured to the outrigger arm 26, it can be secured to the outrigger arm 26 at the desired angle A1 relative to the first guide member 12. The second guide member 30 can be slidably moved along outrigger arm 26 toward and away from the first guide member 12 to adjust the A1 angular orientation of the second guide member 30 relative to the first guide member 12, and once positioned as desired it can be tightened and locked in position using the thumbscrew 32. The second drill guide 49b and the second guide pin 50b can be inserted and advanced through the second guide member 30 as discussed above.

If desired, variations in the method of using the instrument 60 can be employed depending upon surgeon preference. For example, the instrument 60 can be completely assembled prior to deployment and tibial engagement, the order of drilling the tunnels may be varied, the sleeves 40a, 40b may be removed after drilling with pins 50a and 50b or left in place, etc.

With the guide pins 50a, 50b in place in the tibia 100, the instrument 60 can be disengaged from the bone 100. Both of the ratcheted guide pin sleeves 40a, 40b can be rotated 180° to disengage the locking mechanism in the guide members 12, 30 so that the sleeves 40a, 40b can be withdrawn from their respective guide members 12, 30. The outrigger arm 26 can be removed from the first guide member 12 by releasing the thumbscrew 22 and withdrawing the still assembled outrigger 26 and the second guide member 30 over the guide pin 50b. The first guide member 12, along with the attached slider arm 16 and probe arm 10, can be withdrawn over the guide pin 50a, leaving the two guide pins 50a, 50b placed in the tibial bone 100 along intended tibial tunnel trajectories having respective tibial tunnel exit points 106, 108 as shown in FIG. 5.

Tibial tunnels of the desired diameter can then be drilled and reamed over guide pin wires 50a, 50b using conventional cannulated reamers in a conventional manner using conventional surgical drills. FIG. 5 illustrates 5 mm tunnels having a 3 mm offset, although any offset and any size reamers can be used. FIG. 6 shows, by way of non-limiting example, a variety of possible tunnel offset positions using either a 5 mm or 8 mm reamer. In an exemplary embodiment, a kit is provided containing a plurality of outrigger arms, each having a predetermined offset that corresponds to the tunnel offset positions shown in FIG. 6. A person skilled in the art will appreciate that, while the axes of the pathways 13, 31 in the guide members 12, 30 preferably do not intersect, the reamed tunnels can overlap as shown.

Figure 7:
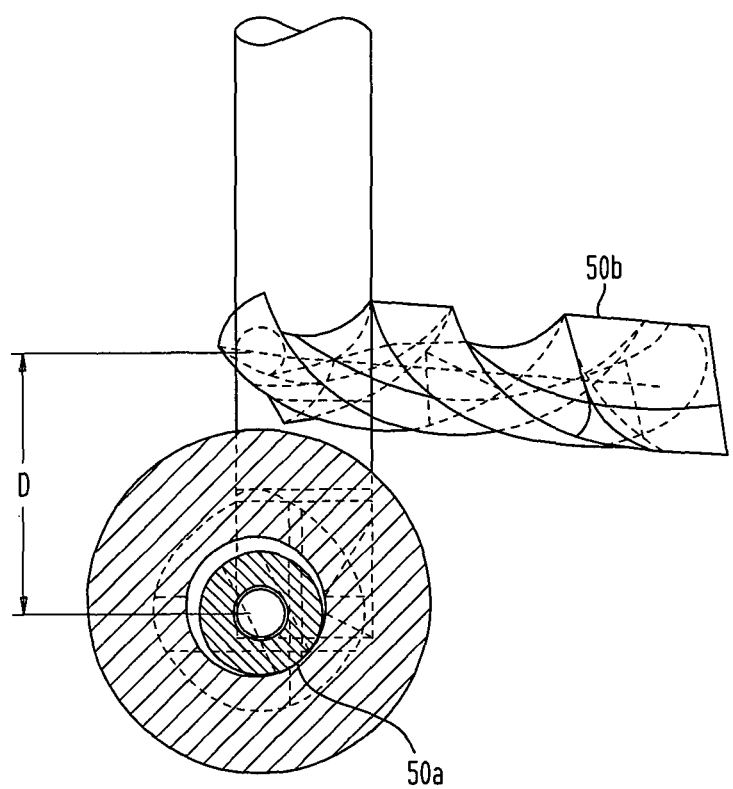
FIG. 7 is a cross-sectional schematic view of a portion of the instrument of FIG. 1.

Because of the angle A1 and vertical offset between the guide members 12, 30, the second guide pin 50b (and hence the second tibial tunnel) can converge toward the first guide pin 50a (and hence the first tibial tunnel), however the axes will not intersect. FIG. 7 illustrates a cross-section of FIG. 3, looking toward the probe arm 10. A distance D can separate the guide pins 50a, 50b, and the distance D can vary based on the offset of the outrigger arm 26 and the position of the second guide member 30 on the outrigger arm 26. By preventing intersection of the axes, overlap between the tunnels formed is minimized or prevented. This is advantageous as the tunnels can each maintain a substantially constant diameter through the entire length thereof, thereby ensuring that the grafts disposed therein will have sufficient freedom to move without impingement by the tunnels. While the offset and the distance D are preferably set to prevent intersection of the axes, the instrument 60 enables a surgeon to allow intersection, such as if the offset is slight enough or is nonexistent. In such a case, it may be advisable for easier maneuverability to slightly withdraw the second guide pin wire 50b prior to reaming the tunnel over the first guide pin wire 50a.

Figure 8:
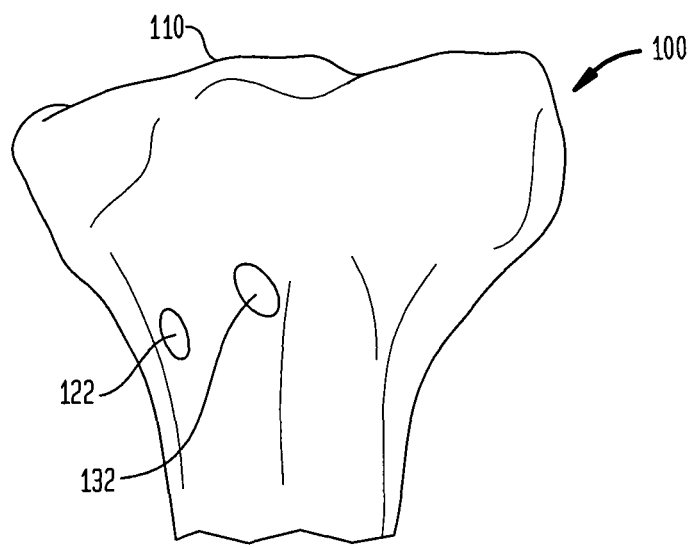
FIG. 8 is a side view of the tibia of FIG. 4 showing entrance holes of dual tunnels drilled in an upper section of the tibia.
Figure 9:
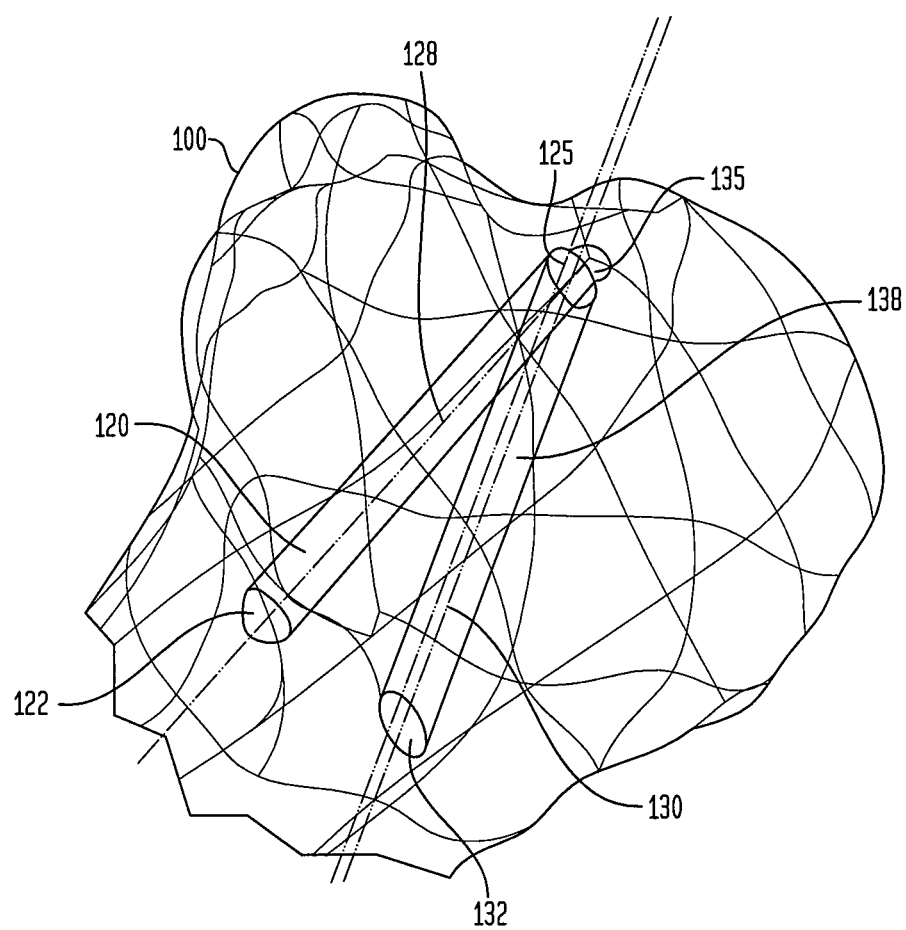
FIG. 9 is a schematic illustration of entrances to tunnels drilled in the tibia of FIG. 4, exits from the tunnels, tunnel trajectories, and a footprint in the tibial plateau.

The end result is first and second tibial tunnels 120, 130 that meet with an offset at the tibial plateau 110 as shown in FIGS. 8-9. The first and second tunnels 120, 130 form, respectively, first and second passageways 128, 138 that extend between first and second entrance openings 122, 132 and first and second exit openings 125, 135.

Figure 10:
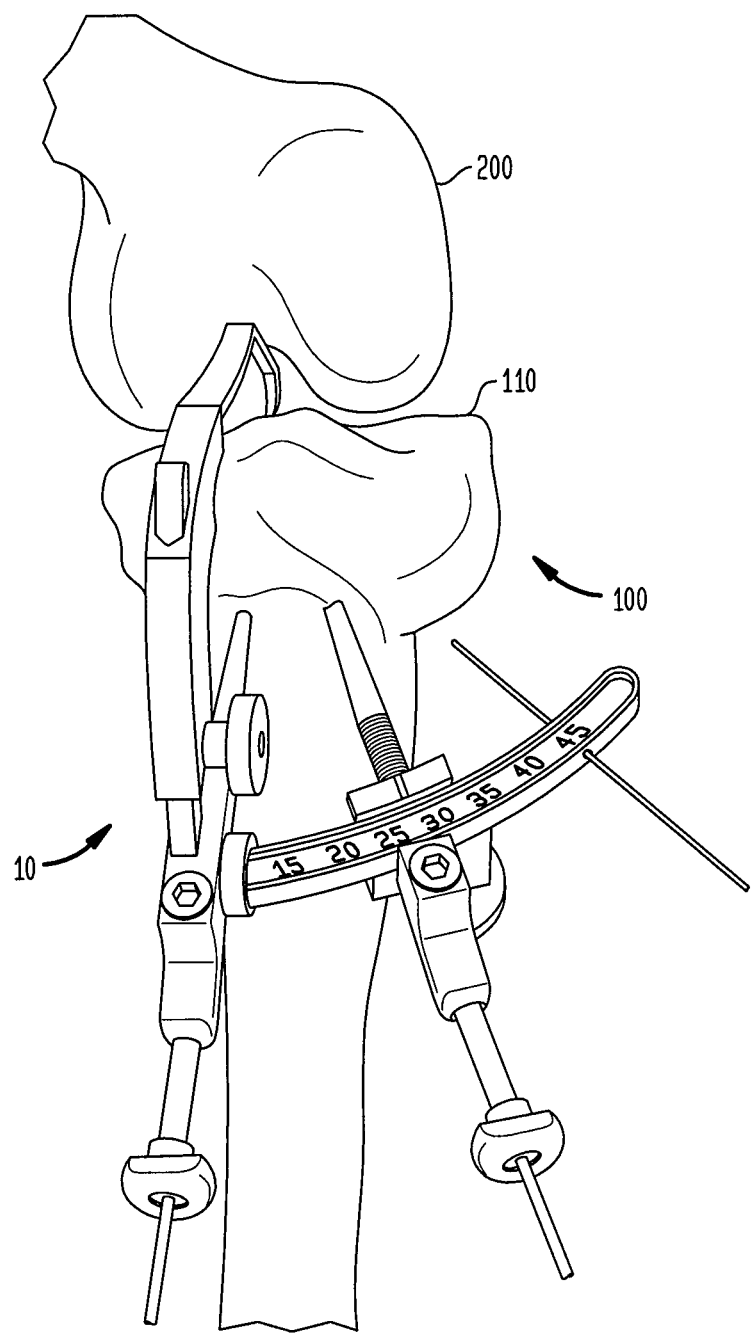
FIG. 10 is a perspective view of the instrument of FIG. 1 engaging the tibia of FIG. 4 and a femur.

Once tibial tunnels 120, 130 are in place, completion of a dual bundle ACL reconstruction can be performed based on individual surgeon preference. As shown in FIG. 10, two femoral tunnels can be created in a femur 200. A currently available conventional femoral offset guide can be used through one of the tibial tunnels 120, 130 to locate a guide pin at the appropriate anatomic position within the femoral notch. A conventional cannulated acorn reamer can be used to create a femoral tunnel of the appropriate depth. A second guide pin, placed either through the second tibial tunnel 130 or an auxiliary arthroscopic portal, can be positioned adjacent to the first femoral tunnel location and a tunnel drilled to the appropriate depth in the same manner as the first.

Graft bundles can next be passed through the tibial tunnels 120, 130 into the femoral tunnels in a conventional manner. A guide pin with an eyelet can be re-introduced through one of the tibial tunnels 120, 130 into the corresponding femoral tunnel and extended along the tunnel axis until the guide pin tip extended through the distal tissue of the lateral thigh. One of the graft bundles can be doubled over a passing suture, the suture can be threaded through the eyelet of the guide pin, and the guide pin can be pulled until the passing suture exited from the skin on the thigh. The passing suture would be used to pull the graft through the tibial tunnel 120, 130 into the femoral tunnel until appropriately seated. The second graft bundle can be passed and seated in the same manner as the first. In the case that an arthroscopic auxiliary portal was used in the creation of the second femoral tunnel, a second guide pin can be reintroduced through the auxiliary portal and an intermediate step of capturing an attached passing loop with a crochet hook or suture grasper inserted through the tibial tunnel 120, 130 and pulling the loop though the tunnel in a retrograde fashion would be required prior to proceeding with passing the second bundle of the graft in the manner described above.

Fixation of the graft in the tibial and femoral tunnels can be accomplished using any of a variety of conventional fixation methods/devices, including but not limited to interference screws, cross pins, sheaths with compression screws, and cortical buttons, posts and screws. One method for anchoring bone grafts in bone tunnels is through a "cross-pinning" technique in which a pin, screw, or rod is driven into the bone transversely to the bone tunnel so as to intersect the bone graft and thereby cross-pin the bone graft in the bone tunnel. In order to provide for proper cross-pinning of the bone graft in the bone tunnel, a drill guide is generally used. The drill guide can ensure that the transverse passage is positioned in the bone so that it will intersect the appropriate tunnel section and the bone graft. The femoral bundles of the graft can be fixed first using the chosen femoral fixation method. The knee can then be flexed to an appropriate position and the bundles can be tensioned to an appropriate amount prior to placement of the tibial fixation devices. With a dual tunnel approach, each of the graft bundles may be tensioned and fixed at different flexion positions and tension levels during the procedure.

A person skilled in the art will appreciate that the various methods and devices disclosed herein can be formed from a variety of materials. Moreover, particular components can be implantable and in such embodiments the components can be formed from various biocompatible materials known in the art. Exemplary biocompatible materials include, by way of non-limiting example, composite plastic materials, biocompatible metals and alloys such as stainless steel, titanium, titanium alloys and cobalt-chromium alloys, and any other material that is biologically compatible and non-toxic to the human body.

One skilled in the art will appreciate further features and advantages based on the above-described embodiments. Accordingly, the description is not to be limited by what has been particularly shown and described, except as indicated by the appended claims.

What is claimed is:

1. A surgical drill guide apparatus, comprising:
a first guide member having a first longitudinal passageway extending therethrough for aiming a first guide pin along a first path to form a first bone tunnel, a second guide member having a second longitudinal passageway extending therethrough for aiming a second guide pin along a second path to form a second bone tunnel, and a support extending between the first and second guide members such that the first and second guide members extend at an angle relative to one another and are offset such that a first longitudinal axis of the first longitudinal passageway and a second longitudinal axis of the second longitudinal passageway do not intersect, the support having a hole formed therethrough for aiming a third guide pin along a third path.

2. The apparatus of claim 1, wherein the support comprises an arcuate support fixedly mated to the first guide member and slidably mated to the second guide member.

3. The apparatus of claim 2, further comprising a second support fixedly mated to the first guide member, the second guide member being selectively slidably matable to the arcuate support and the second support.

4. The apparatus of claim 2, further comprising a plurality of markings formed on the arcuate support for indicating the angle between the first and second guide members.

5. The apparatus of claim 4, wherein the hole is formed adjacent a one of the markings that is a greatest distance away from the first guide member along the support.

6. The apparatus of claim 1, further comprising a tibial engagement member having a proximal end coupled to the first guide member and having a distal end adapted to indicate an exit location of the first bone tunnel formed along the first path.

7. The apparatus of claim 6, wherein the tibial engagement member includes a slider arm mated to the first guide member, and a probe arm slidably disposed along the slider arm, the distal end being formed on the probe arm.

8. The apparatus of claim 1, further comprising a first drill guide mounted in the first longitudinal passageway of the first guide member and a second drill guide mounted in the second longitudinal passageway of the second guide member.

9. The apparatus of claim 8, further comprising markings formed on the first and second drill guides and adapted to indicate a depth of a bone tunnel formed by drill bits disposed through the first and second drill guides.

10. The apparatus of claim 1, wherein the first and second guide members each include a locking mechanism for locking a drill guide slidably disposed in a fixed longitudinal position.

11. The apparatus of claim 1, further comprising a plurality of markings formed on the support for indicating the angle between the first and second guide members, wherein the hole is formed adjacent a one of the markings that is a greatest distance away from the first guide member along the support.

12. A surgical drill guide apparatus, comprising:
a first guide member having a first longitudinal guide passage adapted to receive a first drill guide pin therein to form a first bone tunnel;
a first support arm coupled to and extending horizontally from the first guide member, the first support arm having at least one arcuate section and having a hole formed therethrough that is adapted to receive a third drill guide pin therein; and
a second guide member having a second longitudinal guide passage adapted to receive a second drill guide pin to form a second bone tunnel, the second guide member being slidably disposed along the at least one arcuate section to form a variable angle relative to the first guide member.

13. The apparatus of claim 12, wherein the first support arm is fixedly mated to the first guide member.

14. The apparatus of claim 13, wherein the second guide member is slidable along the first support arm between the first guide member and the hole.

15. The apparatus of claim 12, further comprising a second support arm coupled to and extending vertically from the first guide member, and an engagement member slidably mounted to the second support arm.

16. The apparatus of claim 15, wherein the engagement member has a distal tip adapted to indicate an exit location of bone tunnels formed by drill bits disposed through the first and second guide members.

17. The apparatus of claim 15, wherein the second support arm is fixedly mated to the first guide member.

18. The apparatus of claim 17, wherein the second support arm includes at least one arcuate portion.

19. The apparatus of claim 12, wherein the first and second guide members each have a longitudinal axis, and the axes do not intersect.

20. The apparatus of claim 12, further comprising a first drill guide mounted in the first longitudinal guide passage and a second drill guide mounted in the second longitudinal guide passage.

21. The apparatus of claim 12, wherein the second guide member includes a locking element adapted to lock the second guide member in a position on the at least one arcuate section.

* * * * *